US005776115A

United States Patent [19]
Antoshkiw et al.

[11] Patent Number: 5,776,115
[45] Date of Patent: Jul. 7, 1998

[54] CATHETER HAVING A GEAR-SHAPED LUMEN TO AVERT THE ELIMINATION OF FLUID FLOW THEREIN

[75] Inventors: William Thomas Antoshkiw, Wayne; Joseph Choon Chee, Fort Lee, both of N.J.

[73] Assignee: Becton Dickinson and Company, Franklin Lakes, N.J.

[21] Appl. No.: 587,624

[22] Filed: Jan. 17, 1996

[51] Int. Cl.$^6$ ................................................ A61M 25/00
[52] U.S. Cl. ........................ 604/282; 604/280; 604/264; 128/658
[58] Field of Search ............................. 604/280–282, 604/264, 270; 128/657, 658, 772

[56] References Cited

U.S. PATENT DOCUMENTS

| | | | |
|---|---|---|---|
| 1,596,754 | 8/1926 | Moschelle | 604/282 |
| 3,498,286 | 3/1970 | Palanyi et al. | 604/282 |
| 3,618,613 | 11/1971 | Schulte | 128/348 |
| 3,948,273 | 4/1976 | Sanders | 128/351 |
| 4,027,659 | 6/1977 | Slingluff | 128/2 M |
| 4,351,341 | 9/1982 | Goldberg et al. | 128/348 |

(List continued on next page.)

FOREIGN PATENT DOCUMENTS

| | | |
|---|---|---|
| 0 440 426A1 | 1/1991 | European Pat. Off. |
| 2 607 707A1 | 12/1986 | France. |
| 2 655 548A1 | 12/1989 | France. |
| 1 933 802 | 6/1969 | Germany. |
| 4104092 | 8/1991 | Germany ................ 604/282 |
| 7-59857 | 3/1995 | Japan. |
| 8-24342 | 1/1996 | Japan. |
| WO 92/07507 | 5/1992 | WIPO. |
| 9411057 | 5/1994 | WIPO ..................... 604/280 |

OTHER PUBLICATIONS

"Continuous Spinal Anesthesia" (Donald H. Lambert, Ph.D. M.D., pp. 339–348.

"Strenght of Continuous Spinal Catheters" (Stephen J. Ley, M.D., and Brian R. Jones, M.D) Anesth. Analg. 1991;73:394–6, pp. 394–395.

"A Comparison Between Open–End (Single Hole) and Closed End (Three Lateral Holes) Epidural Catheters", (S. Michael, M.N. Richmond and R. J. S. Birks), Anaesthesia 1989, vol. 44, pp. 578–580.

"A Comparison of Epidural Catheter sWith or Without Subcutaneous Injection Ports for Treatment of Cancer Pain" (Peter C. deJong, M.D. and Peter J. Kansen, M.D.) RegionalAnesthesia and Pain Management, pp. 94–100.

"A Comparison of Two Types of Epidural Catheters" (Stephen H. Rolbin MDCM FRCPC, Ernest Hew MD FRCPC FFARCS (1), Gina Ogilvie, pp. 459–461.

"Introducing the all new Arrow Flex Tip Plus™", 1993.

*Primary Examiner*—Corrine M. McDermott
*Assistant Examiner*—Cris L. Rodriguez
*Attorney, Agent, or Firm*—Arthur D. Dawson

[57] ABSTRACT

A catheter designed for improved patency characteristics under forces normally exerted upon the catheter during use. The catheter features an inner wall having one or more protuberances running lengthwise in a manner parallel with the central axis of the catheter. The protuberances include a tip, a root defined along the inner wall, and a pair of sidewalls extending between the tip and the root. The roots of adjacent protuberances are spaced from one another. A fluid path is established between the inner wall and the opposed sidewalls of adjacent protuberances. The opposed sidewalls can be straight. Alternately, at least one of the opposed sidewalls includes a non-linear portion along its length. In response to a force normally exerted upon the catheter during use, the spacing between adjacent roots and, if so provided, the non-linear portion of an opposed sidewall prevents the opposed sidewalls from entering into total contact with one another, thereby preventing occlusion of the fluid path. If desired, to strengthen the catheter against occlusion by a medical adapter attached to the proximal end, one or more support elements may be incorporated at the proximal end of the inner wall.

4 Claims, 5 Drawing Sheets

U.S. PATENT DOCUMENTS

| | | | |
|---|---|---|---|
| 4,362,163 | 12/1982 | Krick | 604/280 |
| 4,368,730 | 1/1983 | Sharrock | 604/158 |
| 4,469,483 | 9/1984 | Becker et al. | 604/280 |
| 4,610,674 | 9/1986 | Suzuki et al. | 604/282 |
| 4,634,432 | 1/1987 | Kocak | 604/167 |
| 4,723,936 | 2/1988 | Buchbinder et al. | 604/95 |
| 4,737,153 | 4/1988 | Shimamura et al. | 604/282 |
| 4,790,831 | 12/1988 | Skribiski | 604/282 |
| 4,840,623 | 6/1989 | Quackenbush | 604/280 |
| 4,954,129 | 9/1990 | Giuliani et al. | 604/53 |
| 4,955,862 | 9/1990 | Sepetka | 604/164 |
| 4,973,321 | 11/1990 | Michelson | 604/280 |
| 4,985,022 | 1/1991 | Fearnot et al. | 604/282 |
| 4,994,032 | 2/1991 | Sugiyama et al. | 604/96 |
| 5,019,057 | 5/1991 | Truckai | 604/282 |
| 5,057,092 | 10/1991 | Webster, Jr. | 604/282 |
| 5,069,674 | 12/1991 | Fearnot et al. | 604/282 |
| 5,221,257 | 6/1993 | Rosenbloom et al. | 604/53 |
| 5,334,169 | 8/1994 | Brown et al. | 604/282 |
| 5,337,733 | 8/1994 | Bauerfeind et al. | 128/4 |
| 5,380,304 | 1/1995 | Parker | 604/282 |
| 5,423,772 | 6/1995 | Lurie et al. | 604/282 |
| 5,456,674 | 10/1995 | Bos et al. | 604/280 |
| 5,462,523 | 10/1995 | Samson et al. | 604/30 |
| 5,472,435 | 12/1995 | Sutton | 604/282 |
| 5,496,292 | 3/1996 | Burnham | 604/282 |
| 5,593,394 | 1/1997 | Kanesaka et al. | 604/282 |

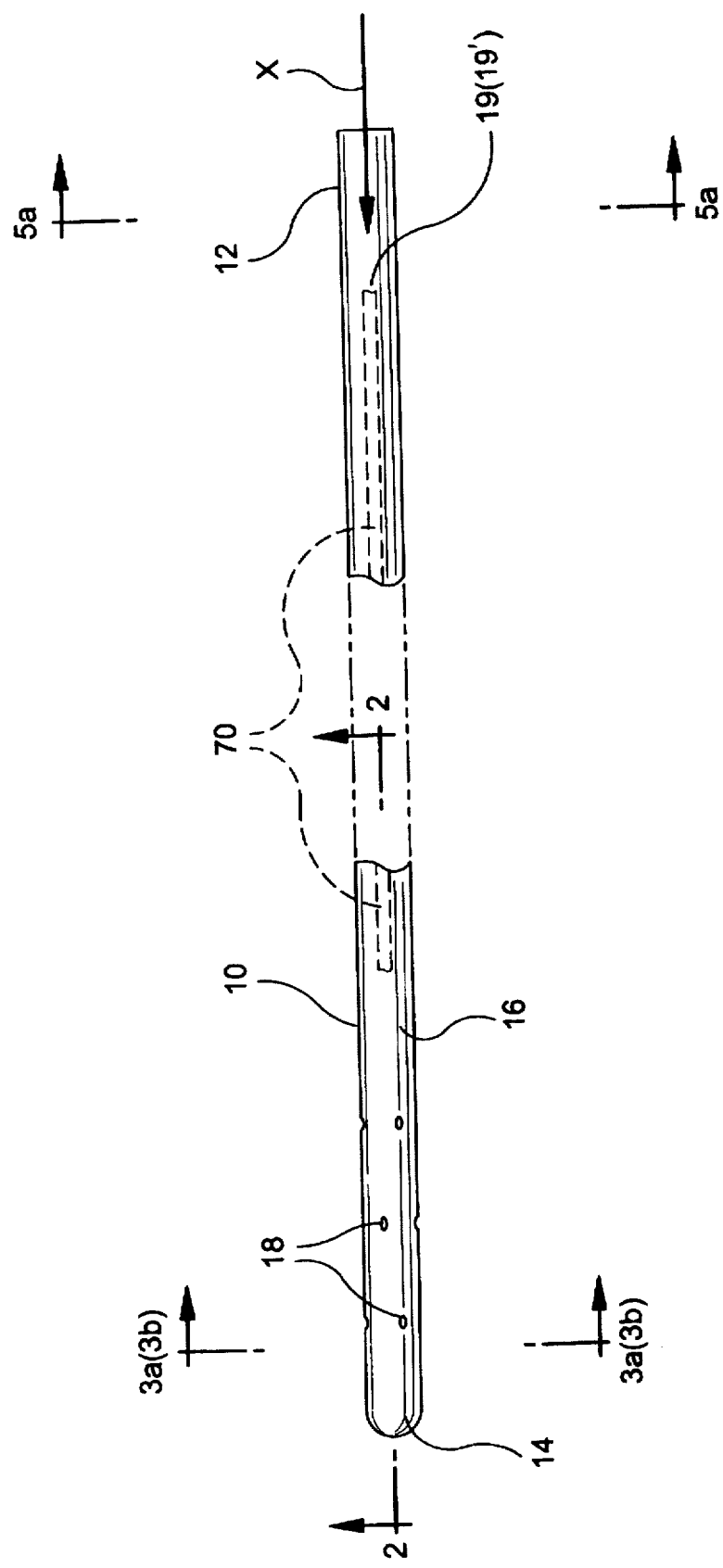

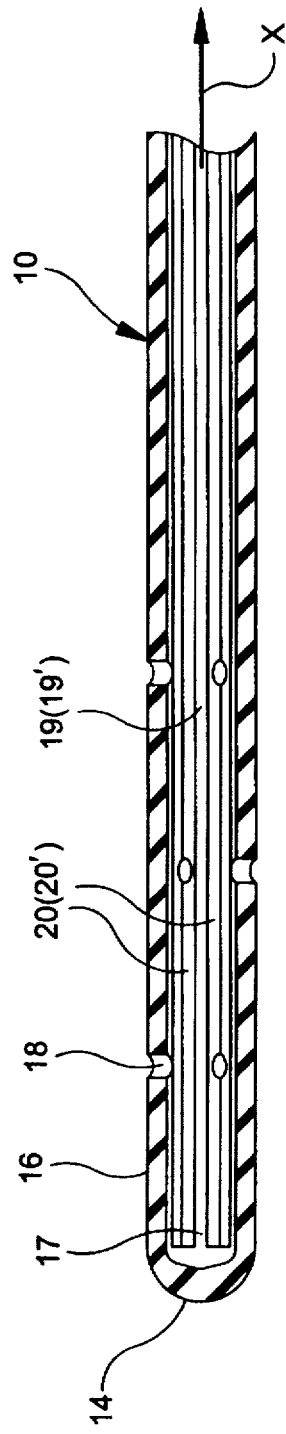
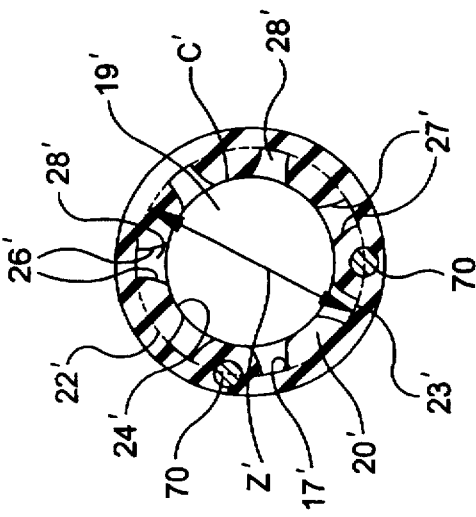
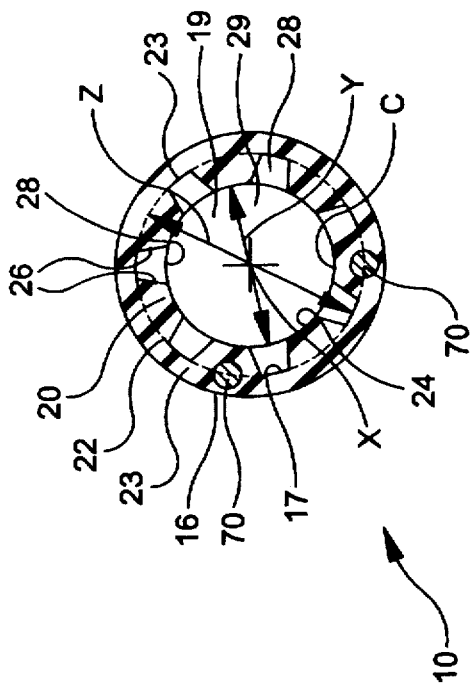

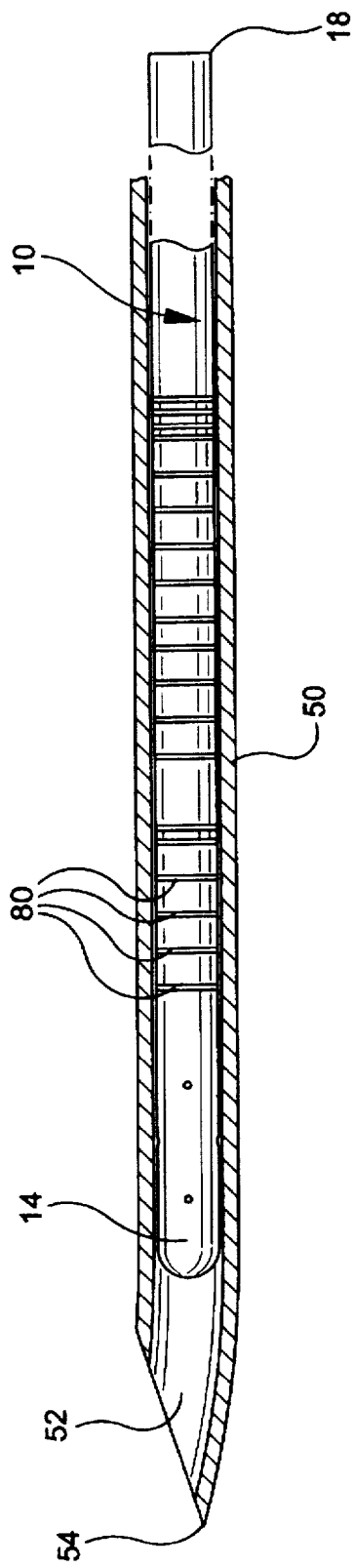
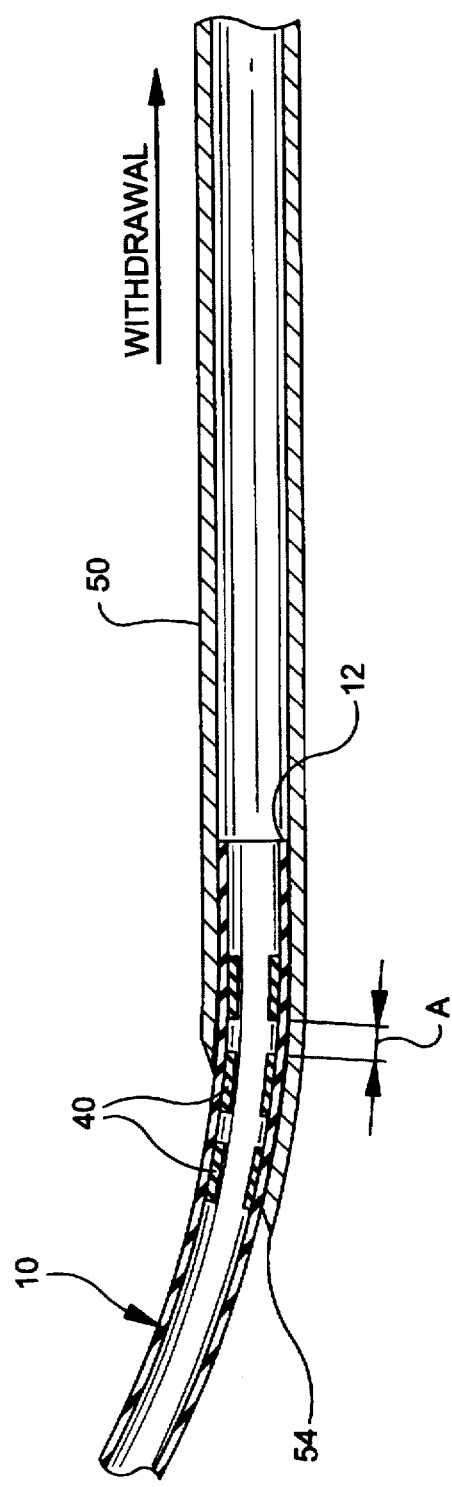

CATHETER HAVING A GEAR-SHAPED LUMEN TO AVERT THE ELIMINATION OF FLUID FLOW THEREIN

FIELD OF THE INVENTION.

This invention relates to a catheter having improved patency characteristics, and more particularly, to a catheter having a gear shaped lumen to avert the elimination of fluid flow through the catheter when subjected to bending or torsional forces and being adaptable for use with standard medical adapter and delivery instruments and accessories.

BACKGROUND

In recent years, there has been a marked increase in the use of catheters by physicians conducting various medical procedures and especially surgical procedures. Catheters are typically elongate tubes formed from medical grade plastics made as polyethylene, polyimide, or even nylon, which define fluid carrying ducts for transporting a medicament from a delivery instrument to body tissue. They are typically introduced into the body cavity through the lumen of a needle or introducer device already pierced into the body. Thereafter, the needle or introducer is threadedly removed about the catheter without displacing the catheter from position within the body. One use of a catheter is found in providing continuous regional anesthesia, and is exemplified, for instance, by the use of epidural catheters to deliver anesthesia to the epidural space of a patient. Catheters are also used for analgesic purposes to provide sustained pain relief following a surgical procedure. Here, the catheter is kept in place following the procedure and analgesic medicaments administered intermittently according to the needs of the patient.

The nature of uses for the aforementioned catheters dictate that dimensions, materials, and other characteristics be selected so as to promote their effective use with minimal trauma or intrusive reaction to the patient. For instance, the outside dimensions of the catheter normally are reduced to as small a diameter as possible so as to minimize the intrusive effects of the catheter to body tissue. Attention must be also paid to the type of material employed for constructing the body of the catheter. In general, catheters such as intended for epidural anesthesia can be formed from a stiff material such as nylon or a soft material such as polyurethane. Both types of materials present certain advantages and certain drawbacks. In a study conducted by M. Johr, F. A. Hess, S. Balogh and H. Gerber, "The choice of the epidural catheter: stiff or soft?" (*Regional Anesthesia*, Volume 17, No. 3S, May–June 1992 Supplement), "stiff" versus "soft" catheters were compared against a number of parameters including difficulty of insertion, sufficiency of the block provided by the catheter, blood aspiration problems, and paraesthesia. In general, it was found that a stiffer catheter might be preferred in view of its easier insertion into the body, but that such catheters provided greater instances of complications including paraesthesia and blood aspiration. Similar conclusions were reached by S. Rolbin, E. Hew, and G. Ogilvie in "A comparison of two types of epidural catheters," Can. J. Anaesth. 1987, 34:5 pp.pp. 459–61. The latter mentioned difficulties such as parasthesia often lead practitioners to prefer catheters made from a softer material so as to minimize trauma caused to the body.

Owing to considerations of diameter and material choice, catheters such as epidural catheters often experience patency difficulties during use. Depending on the forces exerted upon the catheter, the fluid carrying duct defined by the catheter can kink or occlude, particularly at points subject to external pressures such as where a catheter is attached to an injection port site (P. de Long and P. Kansen, "A Comparison of Epidural Catheters With or Without Subcutaneous Injection Ports for Treatment of Cancer Pain," *Anesth. Analg.* 1994, 78: 94–100). The result is the stoppage of fluid flow through the catheter.

For instance, one area of the catheter particularly prone to occlusion difficulties is the proximal end. Here, the catheter is typically secured to a standardized medical connector, such as a Tuohy-Borst adapter, for mating with a medical delivery device such as a syringe. As is well known, the Tuohy-Borst adapter includes a gasket portion which applies pressure about the circumference of the catheter. The pressure exerted at or near the proximal end can cause the catheter walls to collapse upon themselves so as to constrict if not eliminate flow of the medicament from the medical delivery device through the catheter.

Catheters can also experience patency difficulties depending on torsional or bending forces normally exerted upon the catheter while in use. For instance, any twisting or bending action imparted upon the catheter during insertion into the body of a patient might cause the catheter walls to collapse upon themselves, thereby constricting or eliminating fluid flow through the catheter. Also, where the catheter is employed for analgesic purposes, any motions by the patient may cause the catheter to twist or bend, possibly eliminating fluid flow.

Another concern is the practitioner's ability to discern fluid flow through the catheter. Catheters are typically formed from materials that are translucent. Certain attempts in the prior art have sought to strengthen the catheter against collapse, for instance, by incorporating metallic components such as coil windings along the length of the catheter. The presence of a largely opaque metallic component along the catheter length can impede the practitioner's ready view of fluid flow, lessening the practitioner's ability to quickly discern certain difficulties, such as blood aspiration. In view of the exigencies of the operating environment, the need to provide the patient with as rapid and efficient an epidural block as possible, the time constraints on operating room facilities, and the like, such problems cause major difficulties to both patient and medical personnel and they merit address There exists a need, therefore, for a catheter having improved patency characteristics to avert the elimination of fluid flow, which preserves the strength of the catheter as well as the integrity of the catheter in the body, which provides the practitioner with a ready view of the fluids flowing through the catheter, and which in whole addresses the problems experienced by previous approaches.

SUMMARY OF THE INVENTION

These and other concerns are addressed by a catheter according to the present invention. While the principles of the present invention are described with particular reference to a catheter, it will be readily apparent and fully appreciated by the skilled artisan that the principles herein discussed can be readily applied to any tube or similar device subject to patency difficulties.

The catheter is preferably formed from a tube having a proximal end, a distal end, and a length therebetween. The inner wall of a catheter features a plurality of protuberances disposed along the length of the catheter in a manner parallel with the central axis of the tube. The protuberances feature a tip, a root extending along the inner wall of a catheter, and a pair of side walls extending between the tip and the root of the protuberance. The roots of adjacent protuberances are spaced apart from one another along the inner wall, such that each set of opposed sidewalls of adjacent protuberances are separated by a portion of the inner wall. When viewed in cross-section then, the lumen of the catheter gives the appearance of having a gear-shaped profile. A fluid path is established between the inner wall of the tube and each set of opposed side walls of adjacent protuberances. The tip may assume a variety of shapes, such as flat, blunt, rounded, or pointed, as need or desire dictate.

In one configuration, the sidewalls are substantially straight. When bending or torsional forces are exerted upon the catheter, the spacing between the roots of adjacent protuberances prevent the opposed sidewalls of the adjacent protuberances from entering into total contact with one another, thereby avoiding occlusion of the fluid path. If desired, the protuberances may be formed with a tip that is narrower than the root, such that the opposed sidewalls are canted with respect to one another. The canting of the sidewalls, coupled with the spacing of the roots, contributes to the preservation of the fluid path.

In another configuration, at least one of the opposed sidewalls of a protuberance can feature a non-linear portion along its length. For instance, the non-linear portion can be formed as a curved surface defined along the length of the side wall. Preferably, both of the opposed sidewalls of adjacent protuberances feature a non-linear portion along their length. The non-linear portion provided on at least one of the opposed sidewalls, aided by the spacing between the roots, prevents the sidewalls from entering into total contact with one another, thereby safeguarding the fluid path from occlusion.

The catheter can feature a distal end which is either open or closed, as need or desire dictate. One or more side ports can be incorporated adjacent a closed distal end to facilitate fluid delivery into the body. In a preferred embodiment, three side ports are provided.

In order to further strengthen the proximal end of the catheter from constriction by the forces exerted by a medical adapter, such as a Tuohy-Borst adapter, one or more tube-like support elements may be incorporated at the proximal end of the catheter. In one embodiment, the support elements are disposed with the inner wall of the catheter adjacent the proximal end. Preferably, the tubes, which can be formed from sections of metallic or plastic cannulae or from sections of coil windings, are spaced apart from one another within the inner wall of the catheter. By this arrangement, the proximal end of the catheter retains its ability to flex, preventing the proximal end from being caught in the curved distal end of an epidural needle through which the catheter has been threaded.

The catheter may be formed from a variety of materials. Preferably, the material choice is translucent, allowing the practitioner to discern fluid flow through the catheter. One material choice is nylon. Alternately, a soft material such as polyurethane may be employed.

BRIEF DESCRIPTION OF THE DRAWINGS

The invention will now be described in greater detail by way of reference to the following drawings, wherein:

FIG. 1 depicts a longitudinal view of a catheter according to the present invention;

FIG. 2 is a longitudinal cross-sectional view taken along line 2—2 of FIG. 1;

FIG. 3a depicts one way to form the protuberances, as seen in cross-section along line 3a—3a of FIG. 1;

FIG. 3b depicts a second way to form the protuberances, as seen in cross-section along line 3b—3b of FIG. 1;

FIG. 6 is a view in cross-section of a catheter in accordance with the present invention being introduced into the body of a patient by an introducer such as an epidural needle; and FIG. 7 is a view in cross-section of a catheter in accordance with the present invention, wherein an introducer such as an epidural needle is being withdrawn around the catheter once the catheter is finally located in the body.

DETAILED DESCRIPTION OF THE INVENTION

Figure 4:
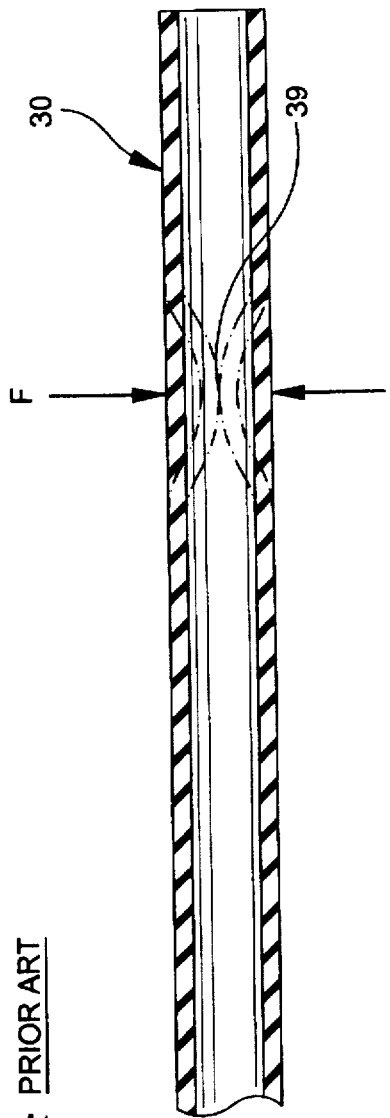
FIG. 4 is a view in cross-section of the proximal end of a prior art catheter subject to constriction by an external force.

Turning now to the drawings, wherein like numerals denote like components, an embodiment of a catheter 10 in accordance with the present invention is depicted in FIGS. 1 and 2. Catheter 10, which may be extruded in tube-like form from a material such as polyurethane or nylon, includes a proximal end 12, a distal end 14 and a length therebetween. Catheter 10 also includes an outer wall 16, an inner wall 17, and a fluid carrying lumen 19 within the catheter characterized by a central axis "X". One or more depth marks 80 (FIG. 6) can be printed or otherwise provided on outer wall 16 to assist the practitioner in assessing the relative insertion of catheter 10 into the body cavity. As herein depicted, distal end 14 is closed, with one or more sideports 18 provided between the outer an inner walls of the catheter, adjacent the distal end, to allow fluid flow between catheter 10 and a body cavity. In a preferred construction, three sideports 18 are provided, but the skilled artisan will appreciate that catheter 10 can be configured to incorporate any number of sideports 18. It will also be realized by the skilled artisan that catheter 10 may be constructed such that distal end 14 is open.

One drawback of certain prior art catheters is their loss of patency owing to occlusion of the fluid duct when torsional or bending forces are applied to the catheter during normal use. A feature of catheter 10 in accordance with the present invention is to incorporate structure which maintains fluid flow through the catheter notwithstanding torsional or bending forces experienced during normal use of the catheter. For instance, as seen in FIGS. 2 and 3a, catheter 10 can be constructed such that fluid carrying lumen 19, when viewed in cross-section (FIG. 3a), appears gear-shaped. Catheter 10 features one or more protuberances 20 formed or otherwise provided along inner wall 17. Protuberances 20 are preferably oriented lengthwise along catheter 10 in a manner parallell with central axis "X" of lumen 19. Here, it will be seen that seven protuberances are provided, but the skilled artisan will appreciate that any number of protruberances appropriate to the size and application of the catheter can be provided. Protuberances 20 each emanate from a root 22 located along inner wall 17 and extend to a tip 24. A pair of sidewalls 26 extend between the tip and root of each protuberance 20.

Fluid carrying lumen 19 is characterized by a main fluid channel 29 and one or more fluid paths 28. Both main fluid channel 29 and each of fluid paths 28 extend along the length of catheter 10. As seen in FIG. 3a, lumen 19 includes a major diameter "Z" as measured at inner wall 17. If a circle "C" is drawn connecting each of tips 24, lumen 19 further defines a minor diameter "Y". The area of catheter 10 located within circle "C" establishes main fluid channel 29 of the lumen. Referring again to FIG. 3a, it will be seen that each of roots 22 of adjacent protuberances 20 are spaced from one another by a respective section 23 of inner wall 17. Accordingly, a fluid path 28 is established, outside of the area of circle "C", between inner wall 17 and each pair of opposed sidewalls 26 of the adjacent protuberances. The overall appearance of lumen 19, when viewed in cross-section, is like that of an internal gear.

The configuration of protuberances 20 preserves the patency of catheter 10 should main fluid channel 29 be subject to occlusion by torsional or bending forces normally experienced during use. Referring to FIG. 5b, if catheter 10 is subjected to torsional or bending forces normally experienced during use, the spacing between roots 22 of the adjacent protuberances prevent opposed sidewalls 26 from entering into total surface contact with one another. Accordingly, fluid path 28 between inner wall 17 and each pair of opposed sidewalls 26 is prevented from total occlusion, thereby permitting fluid flow through catheter 10 even if main fluid channel 29 is occluded by those forces.

FIG. 3a illustrates that sidewalls 26 may be formed substantially straightsided. Here also, it is illustrated that root 22 is wider than tip 24 of a given protuberance 20. Thus, sidewalls 26 are canted between the tip and the root, such that fluid path 28 is wider when measured at circle "C" than it is when measured at inner wall 17. The canting of sidewalls 26, coupled with the spacing provided between roots 22 of adjacent protuberances, contributes to preventing opposed sidewalls 26 from entering into total surface contact with one another under torsional or bending forces. It will, however, be appreciated by the skilled artisan that, if desired, sidewalls 26 need not be canted; roots 22 and tips 24 can assume the same width, with the spacing between roots 22 of adjacent protuberances acting alone to avoid total surface contact between opposed sidewalls 26.

FIG. 3b illustrates an alternate way to configure lumen 19' in accordance with the present invention. Here, in lieu of straight sidewalls 26, each of protuberances 20' feature sidewalls 26' displaying at least one non-linear portion along the length of the sidewall. In one configuration, such as that illustrated in FIG. 3b, the non-linear portion can encompass forming sidewalls 26' with a curved portion 27'. As before, each of protuberances 20' are spaced from one another by a respective section 23' of inner wall 17'. In this manner, curved portion 27', coupled with the spacing provided between roots 22' of adjacent protuberances, helps prevent total surface contact between opposed sidewalls 26', thereby preserving fluid path 28'. Also, as earlier described, sidewalls 26' can be canted between roots 22' which are wider than tips 24', further contributing to preserving the patency of the catheter.

Many of the features of the catheter 10 can be modified by the user as need or desire dictate. For instance, while FIGS. 3a and 3b illustrate that protuberances 20 (20') are evenly spaced along the inner wall, the skilled artisan will appreciate that, if desired, the spacing can be uneven. Also, while the spacing between adjacent protuberances 20 (20') is depicted as sections 23 (23') of the circumferential length of the circular inner wall 17, it will be realized that the catheter can be formed such that sections 23 (23') assume other shapes, whether linear or non-linear. While tips 24(24') are shown as flat, they can assume any shape, such as peaked or rounded, and can either be sharp or blunt, as desired. In addition, while catheter 10 may be extruded from a single material, it will be evident that the catheter can be co-extruded from differing materials. For instance, protuberances 20 (20') may encompass a material differing from the material employed for the rest of catheter 10. Also in this vein, FIGS. 1, 3a and 3b illustrate that one or more radiopaque stripes 70 can be incorporated into catheter 10 by extruding an appropriate material into the body of the catheter. For instance, the one or more radiopaque stripes 70 can be conveniently extruded in the catheter 10 between outer wall 16 and one or more of tips 24 (24') of the protuberances.

As was earlier described, one area of a catheter particularly prone to occlusion difficulties is the proximal end. This is particularly true if the catheter is formed from a relatively soft material such as polyurethane. As illustrated in FIG. 4, in the prior art, a catheter 30 is subject to a torsional and/or pinching forces "F" exerted by a medical adapter, such as a Tuohy-Borst adapter, which is attached to the proximal end. Forces "F" can constrict fluid-carrying lumen 39 of the prior art catheter, contributing to patency difficulties.

Figure 5:
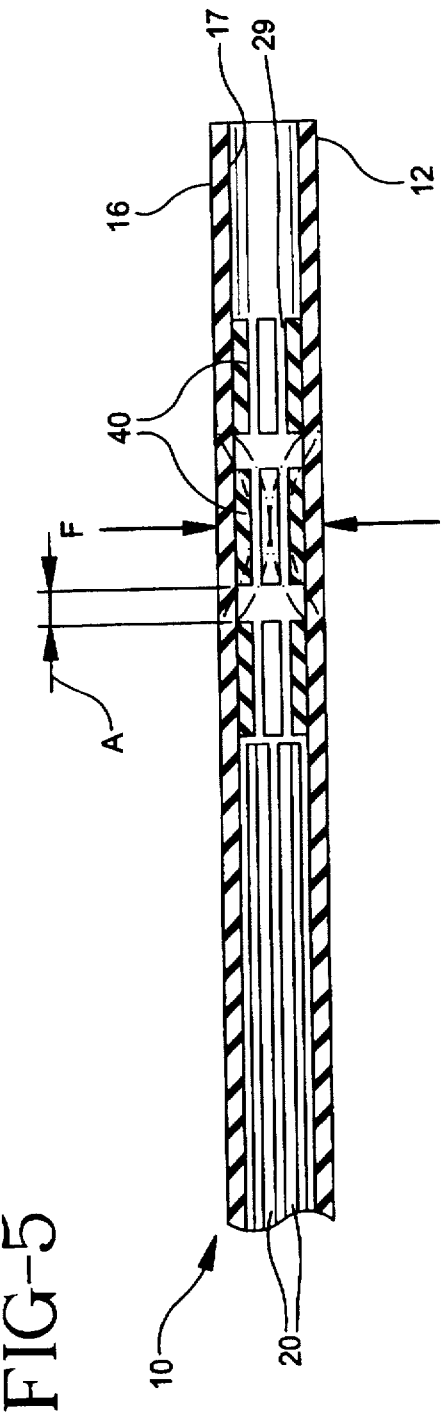
FIG. 5 is a view in cross-section of the proximal end of a catheter in accordance with the present invention, incorporating one or more support elements at the proximal end to avert constriction by an external force.
Figure 5B:
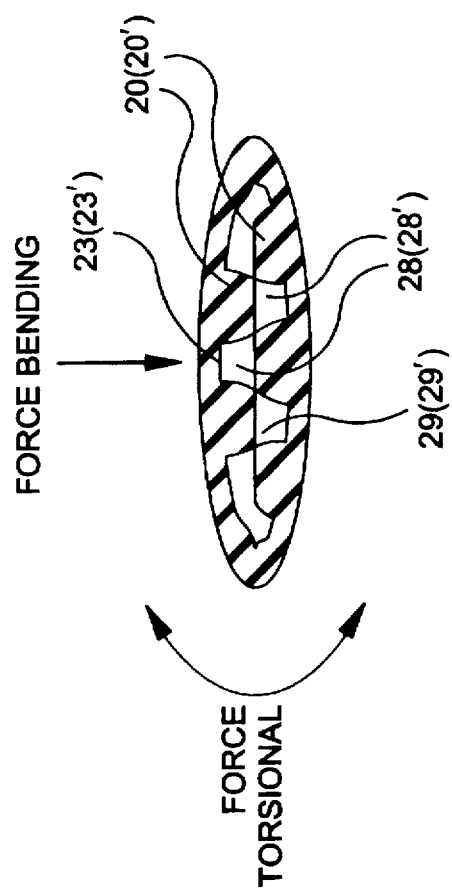
FIG. 5b illustrates, in cross-section, the protuberances acting to preserve the fluid path as the catheter is subjected to forces normally experienced in use.
Figure 5A:
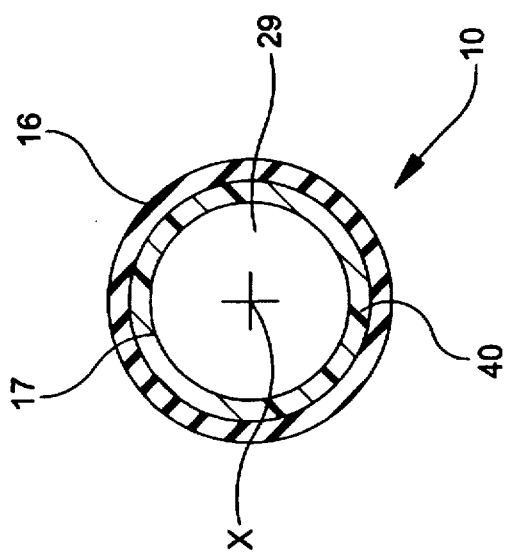
FIG. 5a illustrates support elements which can be incorporated at the proximal end of the catheter, as seen in cross-section along line 5a—5a of FIG. 1; 10

To further enhance the patency characteristics of a catheter in accordance with the present invention, if desired, one or more tube-like support can be inserted into surface contact with inner wall 17 of catheter 10 adjacent the proximal end (see FIGS. 5 and 5a). The support elements, for example, can be formed from sections of metallic or plastic cannulae, or they can encompass sections of coil windings. The number or placement of support elements 40 at the proximal end of catheter 10 may be selected by the user according to the length of catheter 10 subject to forces "F". Here, it will be seen that three support elements 40 are provided. It will also be realized by the skilled artisan that support elements 40 can be incorporated about outer wall 16 of catheter 10.

Preferably, each of the support elements 40 are spaced from one another by a distance "A". As illustrated in FIG. 6, catheter 10 is normally inserted into a patient's body cavity via a lumen 52 of an introducer such as an epidural needle 50. After the catheter is located within the desired area of the body cavity, it is taped or otherwise held in place against the patient, and the epidural needle is withdrawn from the body, with the catheter passing through lumen 52 (see FIG. 7). Most epidural needles 50 include curved distal ends 54. 10 By spacing support elements 40 from one another, proximal end 12 of catheter 10 remains flexible, preventing the proximal end from becoming caught within the curved distal end of epidural needle 50 during withdrawal.

Thus, it will be seen that the catheter according to the present invention addresses many of the drawbacks exemplified by the prior art approaches. The catheter displays improved patency properties substantially along its entire length, all the while not obscuring the view of the practitioner during use and permitting the catheter to be formed from a relatively soft material and with a closed ended construction so as to minimize traumatic effects to the patient. The construction also contributes to overall strength and integrity of the catheter along its entire length.

It will be appreciated and understood by those skilled in the art that further and additional forms of the invention may be devised without departing from the spirit and scope of the appended claims, the invention not being limited to the specific embodiments shown.

What is claimed is:

1. A catheter having patency properties, comprising a tube having a proximal end, a distal end and a length therebetween, said tube defining a fluid path having a central axis, an outer wall and an inner wall, said inner wall having a plurality of protuberances disposed lengthwise on said inner wall in a direction parallel with the central axis of said tube, each of said protuberances having a tip, a root extending along said inner wall, and a pair of straight sidewalls extending between said tip and said root, each of said roots of said plurality of protuberances being spaced a distance from another of said roots of another of said protuberances along said inner wall so that one of said pair of straight sidewalls of said each protuberances faces in opposed relation to one of said sidewalls of another of said protuberances, and wherein in response to a force experienced during normal use of said catheter, said distance between said roots of said plurality of protuberances prevents said opposed straight sidewalls from entering into total contact with one another to prevent occlusion of the fluid path, and wherein at least one of said protuberances further comprises a radiopaque stripe between said outer wall of said tube and said tip of said protuberance.

2. A catheter having patency properties, comprising:

a tube having a proximal end, a distal end and a length therebetween, said tube defining a fluid path having a central axis, an outer wall and an inner wall, said inner wall having a plurality of protuberances disposed lengthwise on said inner wall in a direction parallel with the central axis of said tube, each of said protuberances having a flat tip, a root extending along said inner wall, and a pair of sidewalls each having a non-linear shape extending between said tip and said root, each of said roots of said plurality of protuberances being spaced a distance from another of said roots of another of said protuberances so that one of said sidewalls of said protuberances faces in opposed relation another sidewall of another of each said protuberances, and wherein in response to a force experienced during normal use of said catheter, said non-linear shape of said opposed sidewalls prevents said opposed sidewalls from entering into total contact with one another to prevent occlusion of the fluid path.

3. The catheter of claim 1, wherein said plurality of protuberances comprises seven protuberances.

4. The catheter of claim 1, further comprising three tubes as support elements disposed adjacent the proximal end of said tube, wherein in response to a force applied to the proximal end of said tube, said plurality of support elements prevent said proximal end of said tube from being crushed so as to avert occlusion of the fluid path at said proximal end.

* * * * *